(12) United States Patent
Hsu et al.

(10) Patent No.: US 6,376,218 B1
(45) Date of Patent: Apr. 23, 2002

(54) EXPRESSION SYSTEM FOR PRODUCING RECOMBINANT HUMAN ERYTHROPOIETIN, METHOD FOR PURIFYING SECRETED HUMAN ERYTHROPOIETIN AND USES THEREOF

(75) Inventors: Li-Wei Hsu; Su-Chen Chang, both of Taichung (TW)

(73) Assignee: Research Development Foundation, Carson City, NV (US)

( * ) Notice: Subject to any disclaimer, the term of this patent is extended or adjusted under 35 U.S.C. 154(b) by 0 days.

(21) Appl. No.: 09/206,826

(22) Filed: Dec. 7, 1998

(30) Foreign Application Priority Data

Dec. 31, 1997 (TW) .......................... 86120102 A

(51) Int. Cl.7 .......................... C12N 15/09; C07K 1/16; C07K 1/30; C07K 1/34; C07K 1/36
(52) U.S. Cl. ................... 435/69.4; 435/471; 435/69.1; 530/412; 530/413; 530/417; 530/418
(58) Field of Search .............. 435/69.1, 70.1, 435/71.1, 471, 325, 252.3, 352, 69.4; 530/350, 412, 413, 418, 417

(56) References Cited

U.S. PATENT DOCUMENTS 4,703,008 A * 10/1987 Lin .................... 435/240.2
5,024,939 A * 6/1991 Gorman .................... 435/69.1
5,447,840 A * 9/1995 Blaas et al. .................... 435/5
5,521,283 A * 5/1996 DiMarchi et al.
5,851,808 A * 12/1998 Elledge et al.

OTHER PUBLICATIONS

Hortin et al. Analytical Biochemistry, vol. 188, pp. 271–277, 1990.*

Lee–Huang.., PNAS USA 81:2708–2712, May 1984.*

Tamao Endo, Journal of Chromatography A, vol. 720, pp. 251–261, 1996.*

Jacobs et al., 1985, Nature 313:806–810.*

Tsuda et al., 1990, Eur. J. Biochem. 188:405–411.*

Takeuchi et al., 1990, J. Biol. Chem. 265:12127–12130.*

* cited by examiner

Primary Examiner—Elizabeth C. Kemmerer
(74) Attorney, Agent, or Firm—Benjamin Aaron Adler

(57) ABSTRACT

The present invention provides an expression system for producing recombinant human erythropoietin (rhEPO) exhibiting biological activity and immunochemical properties of the native human erythropoietin (hEPO). Also provided is an improved method for purifying rhEPO from culture medium by two-step column chromatography.

5 Claims, 5 Drawing Sheets

EXPRESSION SYSTEM FOR PRODUCING RECOMBINANT HUMAN ERYTHROPOIETIN, METHOD FOR PURIFYING SECRETED HUMAN ERYTHROPOIETIN AND USES THEREOF

CROSS-REFERENCE TO RELATED APPLICATION

This patent application claims benefit of Taiwanese Patent Application No. 86120102, filed Dec. 31, 1997.

BACKGROUND OF THE INVENTION

1. Field of the Invention

The present invention relates generally to the field of molecular biology of human erythropoietin. More specifically, the present invention relates to an expression system for producing biologically active recombinant human erythropoietin (rhEPO) and an improved method for purifying the secreted rhEPOs.

2. Description of the Related Art

Human erythropoietin (hEPO) is a glycoprotein with molecular weight of 30–40 kD. In healthy adults, mature hEPO is generated in and secreted from kidney. Human erythropoietin mainly functions in enhancing the proliferation of erythropoietin cells in spleen, bone marrow and fetal hepatocytes, and the differentiation of erythrocytes.

Native human erythropoietin was originally prepared from urine of patients with aplastic anemia. The amount of human erythropoietin obtained from the patient's urine is rare, and a traditional process for purifying the human erythropoietin is laborious and time-consuming. Therefore, there is a demand to develop a process for producing and purifying a large amount of human erythropoietin in a simple and economical way.

Genetic engineering techniques using an mammalian cell line as a host for producing a high level of recombinant human erythropoietin (rhEPO) has been developed. A cDNA fragment encoding human erythropoietin was cloned and sequenced by Jacob et al. (Nature, 313: 806–809, 1985). Further, Jacob and colleagues used an expression vector containing a cDNA fragment encoding mature human erythropoietin for transforming kidney fibroblast COS-1 cell under the control of SV40 promoter, and then producing rhEPO from the transformed kidney fibroblast COS-1 cell upon transient expression. Also, Jacob et al. determined the biological activity of produced rhEPO.

U.S. Pat. Nos. 4,703,008, 5,441,868, 5,547,993, 5,621,080, and 6,618,698 disclosed a 5.6 kb genomic DNA fragment containing a full length human erythropoietin gene which was inserted into an expression vector used for transforming monkey fibroblast COS-1 cells. The rhEPO transiently secreted from the transformed monkey fibroblast COS-1 cells could be detected. Further, a stably transformed CHO cell line capable of producing rhEPO could be obtained with the selection of methotrexate. A rhEPO-expressing system in E. coli and yeast was also disclosed.

A baculovirus system in insect SF9 cells was used for producing rhEPO (Quelle et al., Blood 74(2): 652–657, 1989). Although the yield of rhEPO from the transformed SF9 cells was greatly improved (500,000 U/liter culture), the molecular weight of target product was smaller than that of native human erythropoietin due to less glycosylation. Mori and colleagues (Gene 144(2): 289–293, 1994) constructed a rhEPO-expressing vector containing the promoter of interferon-α gene and used the rhEPO-expressing vector for transforming B cell leukemia BALL-1 cells. When transfected with Sendei virus, the transformed B cell leukemia BALL-1 cells could produce rhEPO in a higher level than those transformants obtained by the former investigators.

The method for purifying rhEPO from conditioned medium usually comprises the following steps. Firstly, rhEPO was selectively adsorbed or excluded by passing through an ion-exchange chromatography column, such as DEAE cellulose column (Sherwood and Goldwasser, Endocrinology 103(3): 866–870, 1978) and DEAE Sephacel column (Quelle et al., Blood 74(2): 652–657, 1989; Inoue et al., Biological and Pharmaceutical 17(2): 180–184, 1994; Ben Ghanem et al., Preparative Biochemistry 24(2): 127–142, 1994). Secondly, rhEPO was specifically adsorbed onto immobilized-lectin resin, such as wheat germ agglutinin-agarose (Qian et al., Blood 68(1): 258–262, 1986) and ConA-agarose (Quelle et al., Blood 74(2): 652–657, 1989). Thirdly, C4 reverse phase HPLC was usually employed for purifying rhEPO to homogeneity (Lange et al., Blood Cells 10(2–3): 305–314, 1984; Krystal et al., Blood 67(1): 71–79, 1986; Quelle et al., Blood 74(2): 652–657, 1989; Inoue et al., Biological and Pharmaceutical 17(2): 180–184, 1994). U.S. Pat. No. 5,322,837 disclosed a method of using C4 reverse phase HPLC for preparing rhEPO in homogeneity that exhibits a specific activity of 120,000–160,000 U/mg.

An immobilized monoclonal antibody affinity column was used for the purification of hEPO (or rhEPO). For example, rhEPO secreted from transformed lymphoblastoid cells was specifically adsorbed onto an anti-hEPO monoclonal antibody-Sepharose 4B affinity column (Ben Ghanem et al., Preparative Biochemistry 24(2): 127–142, 1994). The bound rhEPO fraction was eluted, and then passed through a DEAE-Sephacel ion exchange column. A homogeneous product of rhEPO could be obtained with a recovery rate of about 50%.

Although the use of recombinant DNA technology has improved the yield of rhEPO, purification of rhEPO to homogeneity is still laborious and time-consuming, especially when large scale preparation of rhEPO is required.

The prior art is deficient in the lack of effective means of producing a large quantity of rhEPO in an expression system. Further, the prior art is deficient in the lack of effective means of purifying large scale amounts of rhEPO. The present invention fulfills this long-standing need and desire in the art.

SUMMARY OF THE INVENTION

The present invention provides a newly developed expression system for producing rhEPO. Also provided is a novel method of purifying the secreted rhEPOs using a two-step column chromatography technique. For expression of the target protein rhEPO, a PCR-amplified cDNA fragment encoding mature rhEPO was inserted into an expression vector under control of the cytomegalovirus (CMV) promoter. A transformant (BHK-21 cell) harboring the expression vector stably producing and secreting rhEPO with a high yield was obtained under the selection with antibiotic G418. For purification of the rhEPOs, the target proteins were first precipitated from conditioned medium using a salting-out technique. The glycoproteins in the precipitated portion were selectively adsorbed onto immobilized-lectin resin. When bound glycoproteins were eluted with a buffer containing 0.5 M mannose, a pool of rhEPOs was obtained containing major components with molecular weight of around 34 kD and minor components with molecular weight of 35–45 kD. Another pool of rhEPOs persistently bound without being eluted out with the buffer containing 0.5 M mannose could be stripped with an acidic buffer (pH 4.0). The isoforms of rhEPO could be further purified by passing through a G-75 chromatography column.

The purification method disclosed in the present invention provides the following advantages: (1) the target protein rhEPOs are concentrated by precipitation in the first step whereby a large scale preparation of rhEPOs becomes easier, and (2) a pool of rhEPOs with molecular weight of 35–45 kD exhibiting higher specific activity and their isoforms, another pool of rhEPOs with molecular weight of 25–34 kD can be obtained without using reverse phase HPLC or immuno-affinity column chromatography as required by conventional purification methods.

In one embodiment of the present invention, there is provided an expression vector containing a cDNA fragment encoding human erythropoietin and pcDNA3.1 vector under the control of cytomegalovirus promoter. Preferably, the cDNA fragment is produced by PCR using the primers selected from the group consisting of SEQ ID No: 1 and SEQ ID No: 2.

In another embodiment of the present invention, there is provided a cell line harboring the expression vector. Preferably, the cell line is screened by antibiotic G418 resistance. More preferably, the cell line is BHK-21.

In yet another embodiment of the present invention, there is provided a method of producing human erythropoietin by culturing the above mentioned cell line in a conditioned medium and then detecting the production of human erythropoietin. Furthermore, the present invention provides human erythropoietin produced by this method.

In still yet another embodiment of the present invention, there is provided a method for purifying human erythropoietin, comprising the steps of precipitating human erythropoietin from a sample, applying the precipitated human erythropoietin to a n immobilized lectin column and eluting the human erythropoietin from a gel filtration column. Preferably, the resulting purified human erythropoietin contains isoforms with molecular weights of 35–45 kD and has a purity of about 90%.

In still another embodiment of the present invention, there is provided a method for enhancing the proliferation of erythropoietic cells by administering to the cells the human erythropoietin produced by the above mentioned method.

In yet another embodiment of the present invention, there is provided a pharmaceutical composition, comprising the human erythropoietin produced by the above mentioned method and a pharmaceutically acceptable carrier.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

The present invention relates to an expression system comprising an expression vector with a cloned cDNA fragment encoding human erythropoietin in mammalian host cells. The cDNA fragment was amplified by the polymerase chain reaction (PCR). In practice, template DNA fragments encoding human erythropoietin were extracted from a λ phage cDNA library. Two primers (SEQ ID Nos: 1–2) used in PCR reactions were designed according to the sequences published by Jacob and colleagues (Nature 313: 806–809, 1985). A HindIII restriction site was introduced into 5' end of one primer and a XbaI restriction site was added to 3' end of the other primer. The PCR product is expected to be a 596-bp fragment including the coding sequence of the signal peptide. The PCR was performed in the standard procedure. The resultant mixture was extracted by phenol/chloroform and was used as template in the second round of PCR. A fragment of about 600 bp was then obtained and was identified by DNA sequencing analysis.

Figure 1:
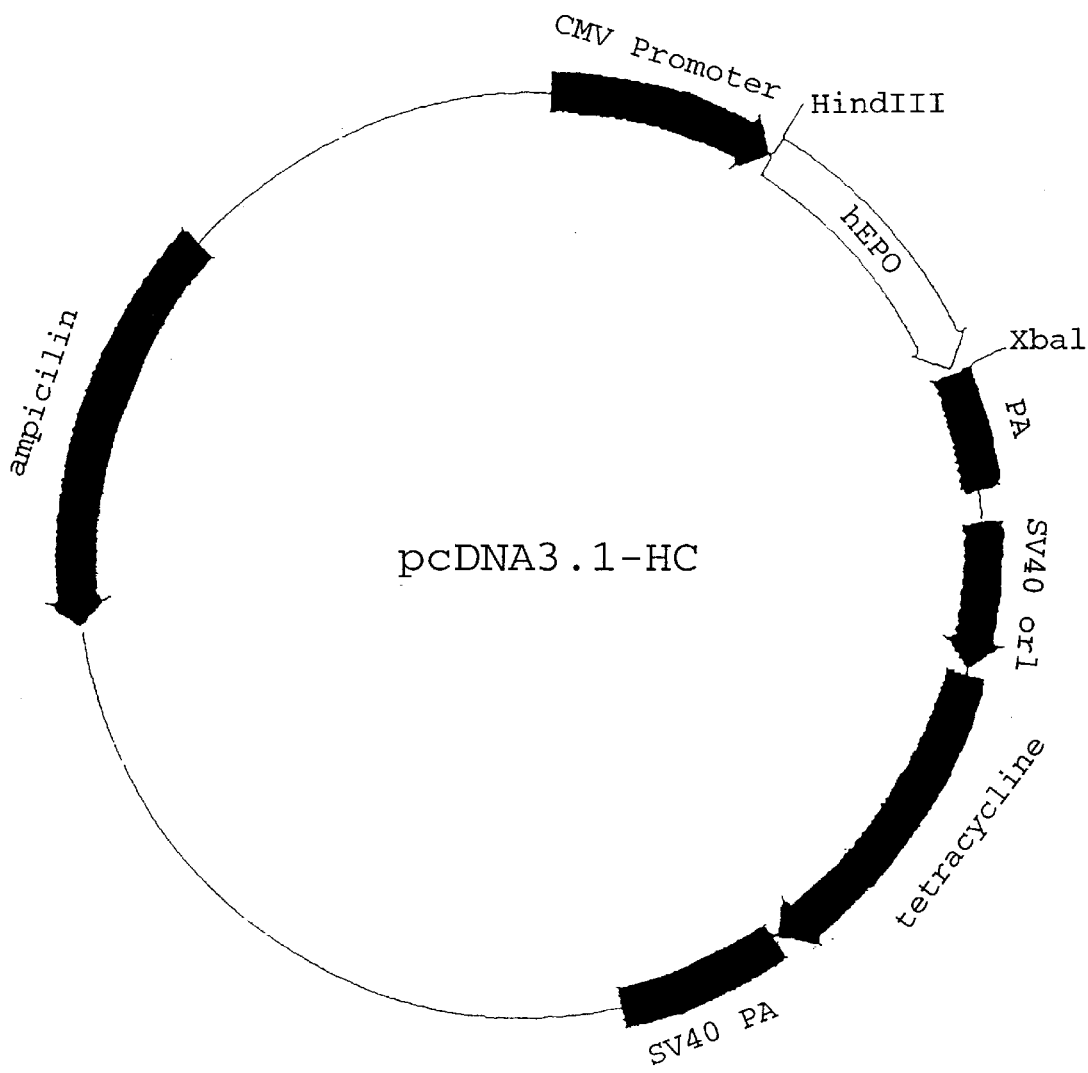
FIG. 1 shows the restriction map of the pcDNA3.1 expression vector for producing rhEPO, namely, pcDNA3.1-HC. The verified human erythropoietin cDNA fragment was ligated into a pcDNA3.1 vector (purchased from Novagene) within HindIII and XbaI restriction sites.

The verified human erythropoietin cDNA fragment was ligated into a pcDNA3.1 vector (purchased from Novagene) within HindIII and XbaI restriction sites. The pcDNA3.1 expression vector for producing rhEPO was prepared and referred to as pcDNA3.1-HC (ATCC Patent Deposit Designation PTA-420) whose restriction map is shown in FIG. 1. The expression of cloned cDNA was under the control of the CMV promoter. A host strain of *E. coli* (Nova Blue) was transformed with the constructed expression vector for producing a transformant.

The present invention also provides a rhEPO-secreting mammalian cell line. The pcDNA3.1-HC was used for transforming baby hamster kidney fibroblast BHK-21 cells (ATCC CCL-10) by employing electroporation. The BHK-21 transformants were screened with various concentrations of antibiotics G418 in a range of 100–400 mg/ml. The G418-resistant foci were picked and expanded. The clone secreting the highest level of rhEPO was referred to as BHK21-pcDNA3.1-HC (ATCC Patent Deposit Designation PTA-419). The biological activity of rhEPO secreted from BHK21-pcDNA3.1-HC was determined by evaluating its ability to enhance the proliferation of the erythroleukemic cell TF-1. In addition, Western blotting analysis and ELISA were employed to verify the immunochemical properties of secreted rhEPO.

The present invention provides a newly developed method to fractionate the rhEPO isoforms secreted from a cell line such as BHK21-pcDNA3.1-HC without using reverse phase HPLC. In this method, the target rhEPOs were first precipitated using a salting out technique. Various amounts of ammonium sulfate (m/v) were added into the conditioned medium and the fractionated pools were collected and analyzed by dot blotting analysis, revealing that all of the target rhEPOs can be precipitated if the saturation of ammonium sulfate reaches between 50% to 80%. Secondly, the collected fractions were incubated with immobilized-lectin resin and the glycoproteins containing target rhEPOs were adsorbed. The buffer used for stripping the bound proteins contained an increased gradient of mannose with a concentration of up to 0.5 M. The persistently bound fraction was thereafter eluted with an acidic buffer (pH 4.0). Both of the pools collected exhibited biological activity and immunochemical properties of rhEPO. Thirdly, each of the collected pools was concentrated and then passed through a Sephadex G-75 column. The mannose-eluted fraction contains a pool of rhEPOs comprising three major components with molecular weight of around 34 kD and minor components with molecular weight of 35–45 kD. This pool of rhEPOs showed a purity of about 90% and exhibited a specific activity of up to 240,000 U/mg, whose specific activity is equivalent to the specific activity to TF-1 cells calibrated by the biological activity of rhEPO produced from CHO cells. The acid-eluted portion contains three major rhEPO isoforms with molecular weight of 34 kD, 28 kD, and 25 kD, and can be purified to homogeneity via Sephadex G-75 column chromatography. Such rhEPO isoforms exhibit lower specific activity than those rhEPOs obtained from the mannose-eluted pool (80,000~12400 units/mg).

In one embodiment of the present invention, there is provided an expression vector containing a cDNA fragment encoding human erythropoietin and pcDNA3.1 vector under the control of cytomegalovirus promoter. Preferably, the cDNA fragment is produced by PCR using the primers selected from the group consisting of SEQ ID No: 1 and SEQ ID No: 2.

In another embodiment of the present invention, there is provided a cell line harboring the expression vector. Preferably, the 20 cell line is screened by antibiotic G418 resistance. More preferably, the cell line is BHK-21.

In yet another embodiment of the present invention, there is provided a method of producing human erythropoietin by culturing the above mentioned cell line in a conditioned medium and then detecting the production. Preferably, human erythropoietin produced by this method is provided.

In still yet another embodiment of the present invention, there is provided a method for purifying human erythropoietin, comprising the steps of precipitating human erythropoietin from a sample, applying the precipitated human erythropoietin to an immobilized lectin column and eluting the human erythropoietin from a gel filtration column. Preferably, the resulting purified human erythropoietin contains isoforms with molecular weights of 35–45 kD and has a purity of about 90%.

In still another embodiment of the present invention, there is provided a method for enhancing the proliferation of erythropoietic cells by administering to the cells the human erythropoietin produced by the above mentioned method.

In yet another embodiment of the present invention, there is provided a pharmaceutical composition, comprising the human erythropoietin produced by the above mentioned method and a pharmaceutically acceptable carrier.

The following examples are given for the purpose of illustrating various embodiments of the invention and are not meant to limit the present invention in any fashion.

EXAMPLE 1

Amplification of cDNA Fragment Encoding hEPO

A template cDNA used in PCR was extracted with phenol/chloroform from human liver cDNA library (ClonTech, catalog no. HL3006a). The primers used in PCR were designed according to the published sequences (Jacob. et al., *Nature* 313: 806–809, 1985) shown below:

EPOS: 5'-GCAAGCTTATGGGGGTGCACGAATG-3' (SEQ ID No: 1)
EPOX: 5'-GCATCTAGATCATCTGTCCCCTGTCCT-3' (SEQ ID No: 2)

The primer EPOS contains a translational initiation codon followed by an introduced HindIII restriction site. The primer EPOX is a sequence at the end of coding sequence terminated with a translational stop codon, to which a XbaI restriction site was added. The mixture for the first round of PCR comprises 1 ml of the template cDNA previously prepared, 1 ml of each of the primers (0.5 mM), 10 ml reaction buffer, 0.5 ml (1.25 units) of Ex Taq DNA polymerase (Takara, Japan), and enough water to meet a final volume of 100 ml. The reaction mixture was heated at 95° C. for 5 minutes prior to proceeding regular thermal cycles. Subsequently, the mixture was denatured at 95° C. for 1 minute, then at 50° C. for 1 minute and finally at 72° C. for 3 minutes. The thermal step was reiterated for 30 cycles, and the product was incubated at 72° C. for 7 minutes for completing the final polymerization. The PCR profile was performed under the control of "Touch Down" thermal cycler (Hybaid). The product was extracted and then prepared for use as a template DNA for another round of PCR. The thermal cycle in the second round of PCR is similar to that in the precious profile, except that the annealing temperature is changed to 52° C. The resultant product was analyzed with 1.5% agarose gel electrophoresis. The amplified DNA fragment with the size of about 600 bp was obtained and verified by DNA sequencing.

EXAMPLE 2

Construction of hEPO Expression Vector (pcDNA3.1-HC)

Both the gel-purified DNA fragment obtained from Example 1 and pcDNA3.1 (Invitrogen) were cleaved by restriction enzymes HindIII and XbaI. The digested DNA fragments were fractionated by gel electrophoresis on agarose gel and were then extracted. The ligation mixture contained 50 ng of PCR-amplified DNA fragment and 20 ng of pcDNA3.1 vector. The ligated product was identified by DNA sequencing technique and was referred to as pcDNA3.1-HC, whose restriction map is shown in FIG. 1. The pcDNA3.1-HC was transformed into NovaBlue (Novagen) competent cells, and the clones with both of ampicillin (100 mg/ml) and tetracycline (25 mg/ml) resistance were selected.

EXAMPLE 3

Cloning of rhEPO-Expressing Mammalian Host BHK21-pcDNA3.1-HC

The cell line BHK-21 (ATCC CCL-10) grew in the standard DMEM medium containing 10% fetal bovine serum. For conducting the transformation, $10^7$ BHK-21 cells were suspended within 0.8 ml PBS buffer (10 mM phosphate buffer, pH 7.2) and then electroporated with 10 mg of cDNA3.1-HC (Gene Pulser II system, BioRad). The resultant cell suspension was diluted with 10 ml of the standard DMEM medium. The transformed BHK-21 cells were cultured in the DMEM medium normally used in the first 24 hours and subsequently in the fresh DMEM medium containing G418 (400 mg/ml). The clones with resistance to G418 were selected and then expanded in the same medium.

The conditioned medium was collected from each of the clones and the biological activity of secreted rhEPO was determined by evaluating its ability to enhance the proliferation of erythroleukemic TF-1 cells (ATCC CRL-2003; Kitamura et al., *J. Cell Physiol.* 140: 323–334, 1989). Normally, TF-1 cells grew in RPMI1640 medium in the presence of recombinant human GM-CSF (rhGM-CSF, 2 pg/ml, R&D System). For performing the proliferation assay on 96-well plate, $10^3$ of TF-1 cells were suspended within 50 ml RPMI1640 medium with no rhGM-CSF, to which the conditioned medium collected from each of the clone culture was then added. The plate was incubated under normal conditions for 4 days. Subsequently, the XTT proliferation kit (purchased from Boehringer Mannheim) was added to label the viable TF-1 cells, and the plate was further incubated for another 12–16 hours. The optical density (OD) of the incubated TF-1 cells was determined via an automatic ELISA reader (Anthos 2001) at a wavelength of 492 nm. The background as a reference was the optical density value read at a wavelength of 620 nm. The clone exhibiting the highest proliferation-enhancing ability was selected and referred to as BHK21-pcDNA3.1-HC.

EXAMPLE 4

Biological Activity of rhEPO Secreted by BHK21-pcDNA3.1-HC

The BHK21-pcDNA3.1-HC was seeded ($2 \times 10^4$ cells/ml medium), and grown in a culture medium with G418 for 7 days. The conditioned medium was collected and the following assays were performed subsequently.

Figure 2:
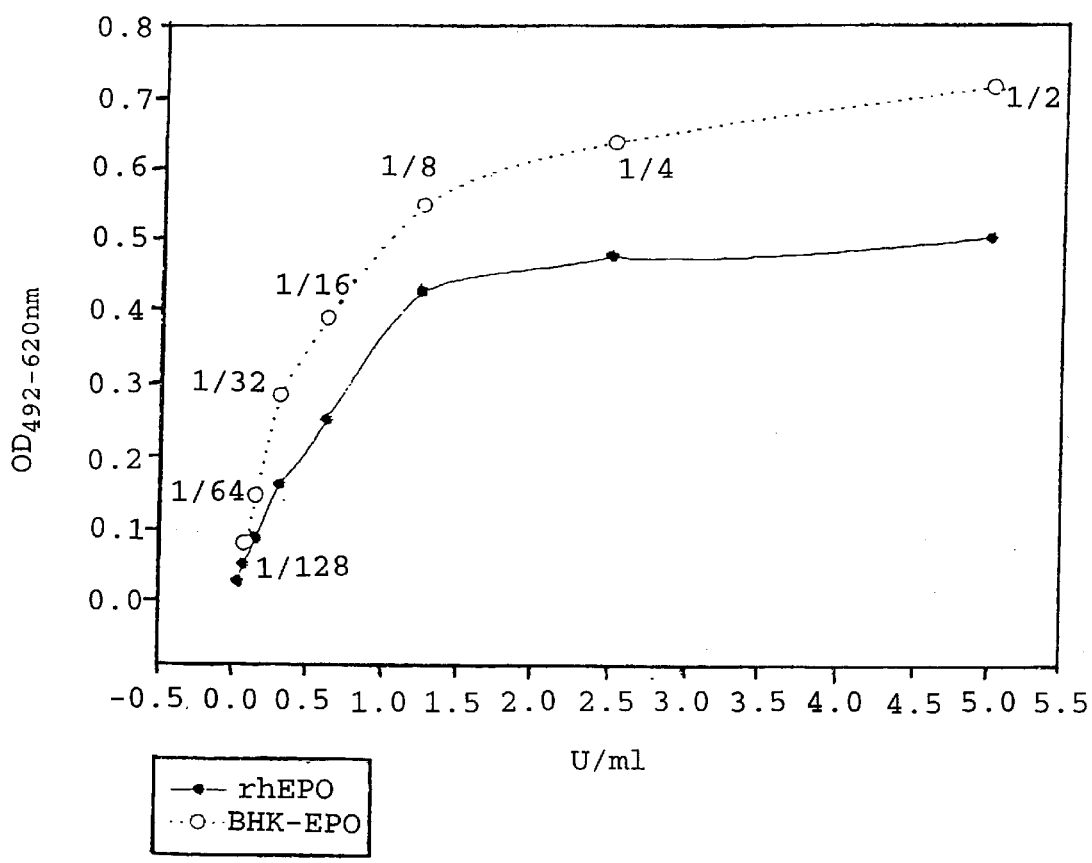
FIG. 2 shows the biological activity of rhEPO secreted by BHK21-pcDNA3.1-HC. Solid circles represent the OD value of purchased rhEPO (standard) after a serial dilution of the medium. Open circles represent the OD value of rhEPO secreted by BHK21-pcDNA3.1-HC, wherein the biological activity was calibrated to a n equivalent value of 19.2 units/ml with the biological activity of rhEPO secreted from CHO cells.

The purchased rhEPO produced from transformed CHO cells has biological activity in enhancing the proliferation of TF-1 cells with $ED_{50}$ value of 0.1–0.5 unit/ml (assayed by $^3$H-thymidine incorporation method). The standard rhEPO was diluted to 5.0, 2.5, 1.25, 0.63, 0.32, 0.16, 0.08 and 0.04 unit/ml for use in the proliferation assay on TF-1 cells. The XTT method as described above was used. The standard curve of $OD_{492-620\ nm}$ value (●) is shown in FIG. 2 and $ED_{50}$ value was calibrated to 0.5 unit/ml.

A serial dilution of 2× of the conditioned medium was used for the proliferation assay under the condition as described above. The curve of $OD_{492-620\ nm}$ value (○) was determined and shown in FIG. 2. The biological activity of rhEPO secreted by BHK21-pcDNA3.1-HC was calibrated to an equivalent value of 19.2 units/ml with the biological activity of rhEPO secreted from CHO cells.

EXAMPLE 5

Immunochemical Property of rhEPO Secreted by BHK21-pcDNA3.1-HC by ELISA

Figure 3:
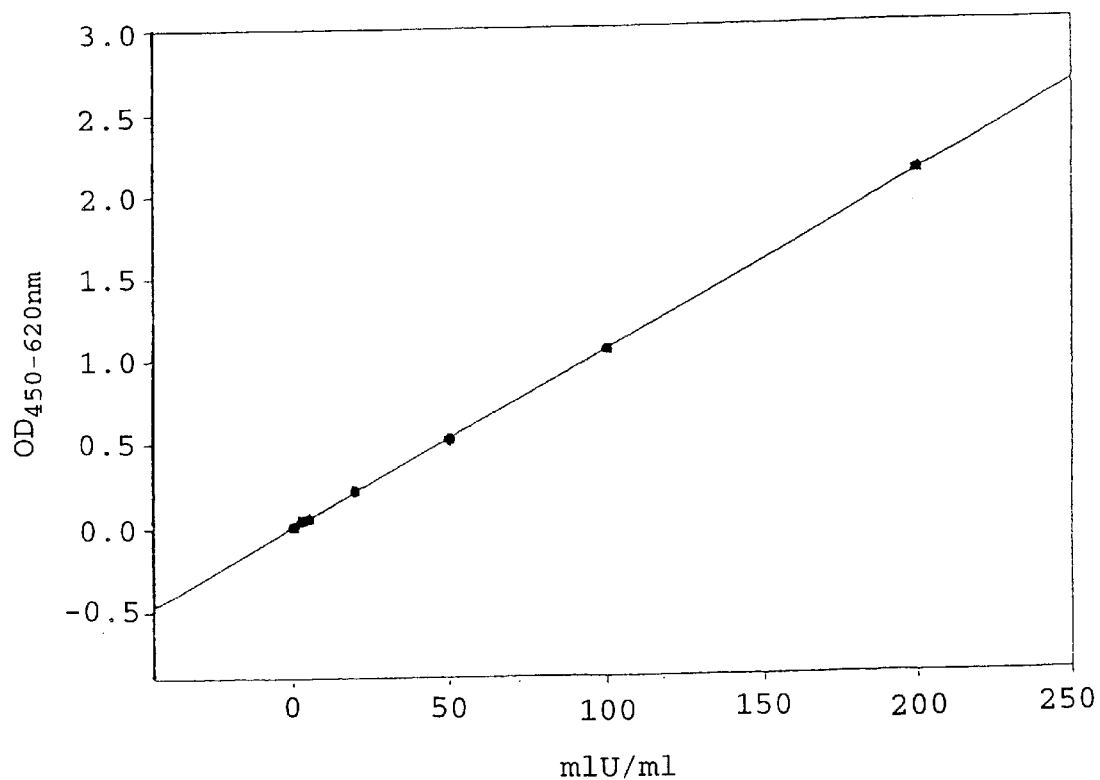
FIG. 3 shows the immunochemical property curve of rhEPO secreted from CHO cells.

An ELISA kit (purchased from R&D system) was used for identifying the immunochemical property of rhEPO secreted from BHK21-pcDNA3.1-HC. The standard rhEPO produced from CHO cells was diluted to a concentration of 200.0, 100.0, 50.0, 20.0, 5.0, 2.5, and 0.0 mIU/ml. The ELISA was performed in accordance with the manufacturer's description. The standard curve of rhEPO secreted from CHO cells is shown in FIG. 3. The rhEPO secreted from BHK21-pcDNA3.1-HC was also serially diluted in a way as mentioned above, and then the ELISA was performed. Based on the $OD_{450-620\ nm}$ value as read, followed by converting the concentration data calculated by interpolation within the standard curve, the average concentration of rhEPO secreted from BHK21-pcDNA3.1-HC was determined 5,886 mIU/ml.

For the biological activity of rhEPO secreted from BHK21-pcDNA3.1-HC as determined above, the result obtained from the enhancement of the proliferation of TF-1 cells is approximately 3 times higher than that obtained from ELISA. Such difference is probably due to the fact that (1) monoclonal antibody specific to the standard rhEPO secreted from CHO cells used in ELISA cannot completely detect the presence of rhEPOs secreted from different transformants, such as BHK21-pcDNA3.1-HC, and (2) there may exist unidentified molecules in the conditioned medium that exhibit a synergistic effect with rhEPO for enhancing the proliferation of TF-1 cells.

EXAMPLE 6

Purification of the rhEPO Secreted from BHK21-pcDNA3.1-HC

In 100 ml of the conditioned medium collected as described above, the total rhEPOs can be salted out by 50–85% gradient saturated ammonium sulfate. The precipitated portion was collected by centrifugation (18,000×g) and the pellet was dissolved in 5 ml of ConA binding buffer (1 mM of $MnCl_2$, $CaCl_2$ and $MgCl_2$ in 10 mM PIPES, pH 6.4). The solution was suspended with 5 ml of ConA-Sepharose and was incubated at room temperature with gentle shaking for at least 2 hours. Subsequently, the mixture was applied onto an immobilized-lectin column, and 100 ml of ConA binding buffer was added for washing. The bound fraction was eluted with 50 ml buffer containing linear gradient mannose up to 0.5 M, and then the persistently bound fraction was eluted with an acidic buffer (0.1 M sodium acetate and 0.5 M NaCl, pH 4.0). The eluted fractions were analyzed on 12% SDS-PAGE gel and rhEPO was verified by the dot blotting analysis.

Figure 4:
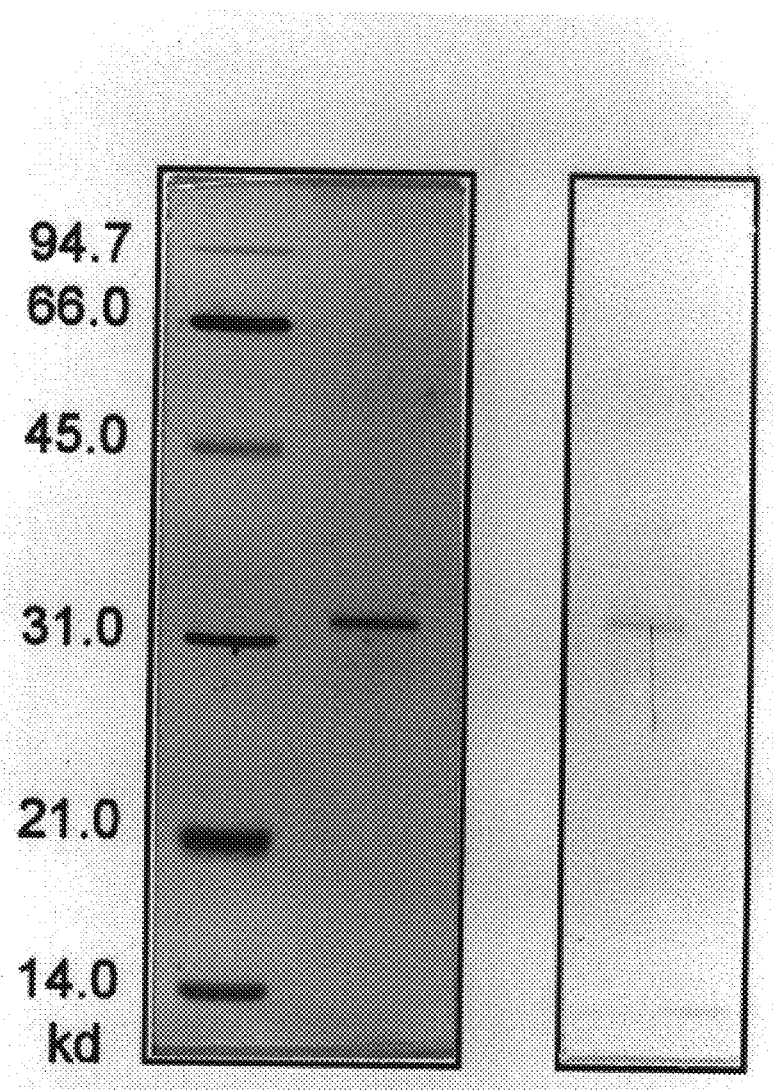
FIG. 4 shows SDS-PAGE-silver-staining and Western blot analysis of the 34 kDa isoform of rhEPO. The homogeneity was obtained by passing the acid-eluted pool through a Sephadex G-75 column.
Figure 5:
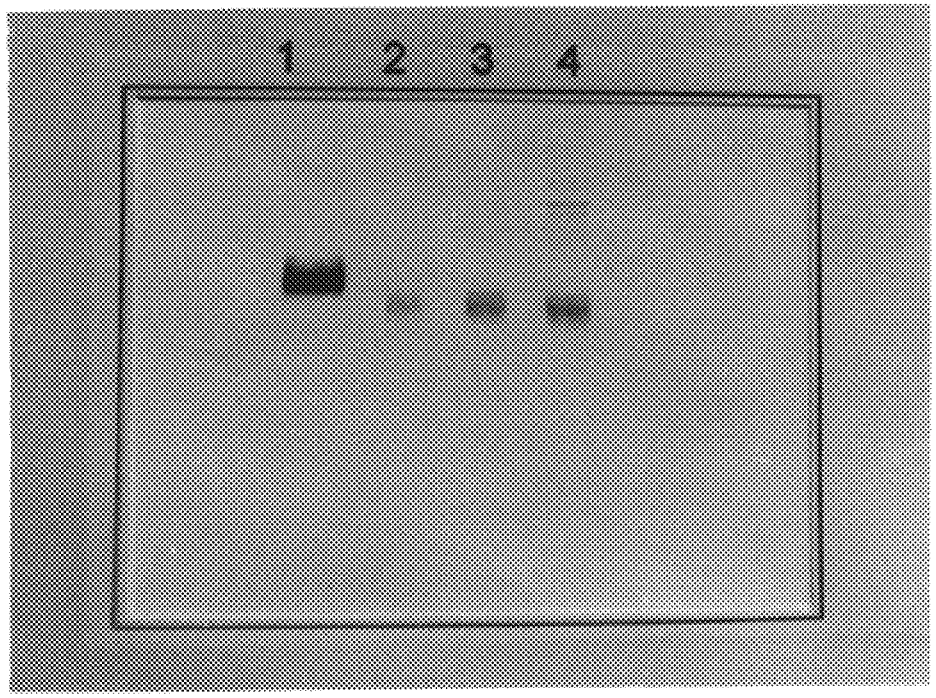
FIG. 5 shows western blot analysis of rhEPO secreted from CHO cells (lane 1) and from BHK21-pcDNA3.1-HC (lanes 2–4). The mannose-eluted pool passes through a Sephadex G-75 column, the fractions containing rhEPO isoforms are continuously collected, part of which are shown in lanes 2–4.

The fractions containing rhEPO eluted out with a mannose gradient buffer or an acidic buffer were respectively pooled together and concentrated with filter membrane (PM 10 membrane, Amicon) until a final volume reaches to about 3 ml. The concentrated solutions were applied onto a column filled with Sephadex-G75 resin (16 mm×100 mm) and PBS buffer as an elution buffer was added. From the mannose-eluted pool, a mixture comprising major rhEPOs with molecular weight of around 35 kD and minor rhEPO isoforms with molecular weight of 36–45 kD can be obtained. This pool of rhEPOs exhibits a combined specific activity of 180,000–240,000 units/mg. Another pool (acid-eluted) contains three major isoforms of rhEPO respectively with molecular weight of 34 kD (124,000 units/mg) which can be homogeneous, with 25 and 28 kD (80,000 units/mg). The result of silver staining and Western blotting analysis is shown in FIGS. 4–5.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of producing substantially purified recombinant human erythropoietin, comprising the steps of:
culturing a baby hamster kidney fibroblast cell line expressing active recombinant human erythropoietin from an expression vector comprising a cDNA fragment encoding human erythropoietin, a plasmid vector pcDNA3.1 and a cytomegalovirus promoter, wherein said cDNA fragment is produced by polymerase chain reaction (PCR) using a primer set comprised of SEQ ID No. 1 and SEQ ID No. 2;
collecting conditioned medium containing said expressed recombinant human erythropoietin from a culture of said baby hamster kidney fibroblast cell line;
precipitating the human erythropoietin from said conditioned medium;
applying a resuspension of precipitated human erythropoietin to an immobilized lectin column;
eluting said human erythropoietin from said immobilized lectin column with an increased mannose gradient solution;
applying eluted human erythropoietin to a gel filtration column; and,
eluting the human erythropoietin from said gel filtration column.

2. The method of claim 1, wherein the purified human erythropoietin contains isoforms with molecular weights of from 35 kD to 45 kD.

3. The method of claim 2, wherein said purified human erythropoietin has a purity of about 90%.

4. The method of claim 1, wherein said baby hamster kidney fibroblast cell line is resistant to antibiotic G418.

5. The method of claim 1, wherein the purified human erythropoietin exhibits a specific activity of up to 180,000 to 240,000 units/mg.

* * * * *

UNITED STATES PATENT AND TRADEMARK OFFICE
CERTIFICATE OF CORRECTION

PATENT NO. : 6,376,218 B1
DATED : April 23, 2002
INVENTOR(S) : Hsu, Li-Wei and Chang, Su-Chen It is certified that error appears in the above-identified patent and that said Letters Patent is hereby corrected as shown below:

<u>Title page,</u>
Item [73], please remove "Research Development Foundation. Carson City, NV (US)" as the assignee. There is no assignee.

Signed and Sealed this

Twenty-ninth Day of October, 2002

*Attest:*

*Attesting Officer*

JAMES E. ROGAN
*Director of the United States Patent and Trademark Office*

SEQUENCE LISTING

<160> NUMBER OF SEQ ID NOS: 2

<210> SEQ ID NO 1
<211> LENGTH: 25
<212> TYPE: DNA
<213> ORGANISM: artificial sequence
<220> FEATURE:
<221> NAME/KEY: primer_bind
<223> OTHER INFORMATION: primer used for PCR
<300> PUBLICATION INFORMATION:
<301> AUTHORS: Jacob. et al.
<302> TITLE:
<303> JOURNAL: Nature
<304> VOLUME: 313
<306> PAGES: 806-809

<400> SEQUENCE: 1
gcaagcttat gggggtgcac gaatg     25

<210> SEQ ID NO 2
<211> LENGTH: 27
<212> TYPE: DNA
<213> ORGANISM: artificial sequence
<220> FEATURE:
<221> NAME/KEY: primer_bind
<223> OTHER INFORMATION: primer used for PCR
<300> PUBLICATION INFORMATION:
<301> AUTHORS: Jacob. et al.
<302> TITLE:
<303> JOURNAL: Nature
<304> VOLUME: 313
<306> PAGES: 806-809

<400> SEQUENCE: 2
gcatctagat catctgtccc ctgtcct     27